United States Patent
Pulido-Cejudo

(10) Patent No.: US 6,521,415 B1
(45) Date of Patent: Feb. 18, 2003

(54) TANDEM IMMUNO-ASSAY FOR CANCER

(75) Inventor: Gabriel Pulido-Cejudo, Ottawa (CA)

(73) Assignees: Canbreal Therodiagnostics Canada Holding Corporation (CA); Her Majesty the Queen in right of Canada, as represented by the Minister of Health (CA)

(*) Notice: Subject to any disclaimer, the term of this patent is extended or adjusted under 35 U.S.C. 154(b) by 0 days.

(21) Appl. No.: 09/538,200

(22) Filed: Mar. 30, 2000

(30) Foreign Application Priority Data

Mar. 30, 1999 (CA) ............................................. 2267481

(51) Int. Cl.[7] ...................... G01N 33/53; G01N 33/574; G01N 33/573; G01N 33/48; C12N 9/00

(52) U.S. Cl. ........................ 435/7.23; 435/7.1; 435/7.4; 435/183; 435/975; 436/64

(58) Field of Search ................................ 435/7.23, 7.4, 435/183, 975, 7.1; 436/64

(56) References Cited

U.S. PATENT DOCUMENTS

| | | | |
|---|---|---|---|
| 5,001,052 A | 3/1991 | Kahan et al. | 435/7.23 |
| 5,179,008 A | 1/1993 | Kahan et al. | 435/70.21 |

FOREIGN PATENT DOCUMENTS

| | | |
|---|---|---|
| CA | 2108533 | 4/1994 |
| WO | 9009397 | 8/1990 |
| WO | 9741441 | 11/1997 |

OTHER PUBLICATIONS

X. Sastre–Garau et al., "Nucleoside Diphosphate Kinase/nm23 Expression in Breast Cancer: Lack of Correlation With Lymph–Node Metastasis," Int. J. Cancer: 50, 533–538 (1992).* van den Oord J J et al., "Prognostic Significance of Nm23 Protein Expression in Malignant Melanoma. An Immunohistochemical Study," Melanoma Research, (Apr. 1997) 7 (2) 121–8.*

Willems, et al., 1998, J Biol Chem, 273(22):13663–68.*

Pulido–Cejudo, Gabrial, et al, "NDP–Kinase And Leucine Aminopeptidase: Two Prognostic Factors Of Cellular Invasiveness and Metastasis of Human Brain Tumours", Journal of Cellular Biochemistry Supplement, (1994) vol. 0, No. 18D, pp. 111. Meeting Info.: Keystone Symposium On Molecular Basis Of Cancer Therapy Tamaron, Colorado, USA Mar. 4–10, 1994, XP000916389.

Database CAPLUS Online! STN; Shikoku Igaku Zasshi, 32(1), pp. 79–93, 1976, Niinobe, Michio: "Studies on Leucine Aminopeptidase In Normal and Cancerous Tissues in Man"; XP002143290.

Lydia L. Nakipolou et al.: "Nm–23, c–erb–2, and Progesterone Receptor Expression in Invasive Breast Cancer: Correlation With Clinicopathologic Parameters"; Cancer Detection and Prevention, vol. 23, No. 4, 1999, pp. 297–308, XP000916390.

PCT International Search Report; PCT Application No. PCT/CA 00/00330; filed Mar. 30, 2000.

Gupta, et al., "Serum Leucine Aminopeptidase Estimation: A Sensitive Prognostic Indicator of Invasiveness in Breast Carcinoma", Indian J. Pathol, Microbiol. 32:4; p. 301–305: 1989.

Toulas, et al., "Potential Prognostic Value in Human Breast Cancer of Cytosolic Nme 1 Protein Detection Using An Original Hen Specific Antibody", British Journal of Cancer (1996) p. 630–635.

Han et al., "Abnormal Expression of Four Novel Molecular Markers Represents a Highly Aggressive Phenotype in Breast Cancer. Immunohistochemical Assay of p53, nm23, erbB–2, and Cathespin D Protein", Journal of Surgical Oncology 1997; 65: 22–27.

Cheng et al.; "Demonstration of the Heterogeneity of Nucleoside Diphosphokinase in Rat Tissues"; *Biochemistry* 1973; 12: 5–10.

Dunzendorfer U. and Drahovsky D.; "Estrogens in Carcinoma of the Prostate: Effects on Enzymes and Nad Polypeptide Hormones.", *Arzneim.–Forsch./Drug Res.* 1978; 28(1), Heft 6:1027–1030.

Gilman A.G..; "G Proteins: Transducers of Receptor–Generated Signals"; *Ann.Rev.Biochem.* 1987; 56:615–649.

(List continued on next page.)

*Primary Examiner*—Sheela Huff
*Assistant Examiner*—Natalie Davis
(74) *Attorney, Agent, or Firm*—Thompson Hine LLP

(57) ABSTRACT

The identification and characterization of risk factors and their molecular implications in the pathophysiology of human diseases such as cancer is essential for designing efficient diagnostic assays and therapeutic compounds. Estrogenic steroids, under normal physiological conditions, have been shown to play a critical function in several tissues. The response of such a variety of tissues to estrogen stimulation can explain in part its active role in the development and progression of different human diseases, particularly breast cancer. Searching for estrogen-responding cellular factors in parental cells of primary human breast carcinomas obtained from tumour biopsies, two cellular markers, an isoenzyme of putative leucine aminopeptidase (LAPase; EC 3.4.11.1) from parental cells of primary human breast carcinomas obtained from tumour biopsies, and cytosolic NDP-Kinase/Nm23 (EC 2.7.4.6) from HL60 cells were identified. Monoclonal antibodies against each cellular marker have been produced. Determination of the presence of these two markers, either alone or in combination, -can be used to detect breast cancer, and in particular, associated metastasis. Thus, this invention refers to the use of both LAP and NDP-Kinase/Nm23 monoclonal antibodies together in a tandem solid-matrix based immuno-assay for first line confimatory blood-based testing for breast cancer.

5 Claims, 3 Drawing Sheets

OTHER PUBLICATIONS

Gupta S.K. et al.; "Serum Leucine Aminopeptidase Estimation: A Sensitive Prognostic Indicator of Invasiveness in Breast Carcinoma."; *Indian J Pathol Microbiol* Oct.; 1989 32(4):301–305.

Igawa, M., Rukstalis, D.B., Tanabe, T., and Chodak, G.W. (1994) "High Levels of nm23 Expression Are Related to Cell Proliferation in Human Prostate Cancer". *Cancer Research*, 54: 1313–1318.

Kimura and Shimada; "GTP–Activated GTP Binding Protein (Gs) in Membranes Achieved By Hormone Plus GDP Does Not Serve As A Substrate For ADP–Ribosylation By Cholera Toxin"; *Biochemical and Biophysical Research Communications*, 1986; 134: 928–936.

Kimura and Shimada; "GDP Does Not Mediate but Rather Inhibits Hormonal Signal to Adenylate Cyclase"; *The Journal of Biological Chemistry* 1983; 258: 2278–2283.

Kimura and Shimada; "Membrane–associated Nucleoside Diphosphate Kinase from Rat Liver"; *The Journal of Biological Chemistry* 1988; 263: 4647–4653.

Kobayashi H. et al.; "[The Significance of Serum Leucine Aminopeptidase (P–LAP) Determination in the Gynecological Malignancies]."; *Nippon Sanka Fujinka Gakkai Zasshi* May 1985; 37(5):696–702.

Kobayashi, S., Iwase, H., Itoh, Y., Fukuoka H., Yamashita, H., Kuzushima T., Iwata, H., Masaoka A., and Kimura N. "Estrogen Receptor, c–erB–2 and nm23/NDP Kinase Expression in the Intraductal and Invasive Components of Human Breast Cancers". *Jpn. J. Cancer Res.* Aug. 1992; 83(8):859–865.

Partanen S. and Syrjanen K.; "Histochemically Demonstrable Enzyme Activtivies and Their Independence of the Hormone Receptor Content in Female Breast Carcinoma."; *Histopathology*, 1982,6: 771–777.

Prall, O.W.J. et al.; "Estrogen–induced Activation of Cdk4 and Cdk2 during $G_1$–S Phase Progression Is Accompanied by Increased Cyclin D1 Expression and Decreased Cyclin–dependent Kinase Inhibitor Association with Cyclin E–Cdk2"; *The Journal of Biological Chemistry* 1997; 272; pp. 10882–10894.

Pulido–Cejudo Gabriel et al.; "Critical Interdependency: From the Role of Estrogen on Breast Cancer to the Susceptibility of Women Towards HIV Infection."; *Intermolecular Cross–Talk in Tumor Metastasis;* Series A: Life Sciences– vol 311; Skouteris George G. and Nicolson Garth L.; IOS Press, 1999; Washington, D.C. p. 123–136.

Pulido–Cejudo Gabriel et al.; "Increase Expression of Leucine Aminopeptidase in Human Breast Carcinoma Cell Lines: A Target for Combined Chemokine Therapy." Abstract presented at the Keystone Symposia on Molecular and Cellular Biology; Feb. 4, 1997; Abstract No. 324, Sec.: Development of Immunotherapies.

Pulido–Cejudo et al,; "Measurement of Nucleoside Diphosphate Kinase–Nm23 Activity by Annion–Exchange High–Performance Liquid Chromatography"; *Journal of Chromatography B.* 1994; 660: 37–47.

Sawan A.; Lascu I., Veron M., Anderson J.J., Wright C., Horne C.H., and Angus B., "NPD–K/nm23 Expression in Human Breast Cancer in Relation to Release, Survival, and Other Prognositc Factors: An Immunohistochemical Study". *Journal of Pathology* Jan.; 1994 172(1): 27–34.

Shekhar, P.V.M., Werdell J., and Basrur V.S. (1997). "Environmental Estrogen Stimulation of Growth and Estrogen Receptor Function in Preneoplastic and Cancerous Human Breast Cell Lines". *Journal of the National Cancer Institute*, 89: 1774–1782.

Srivatsa P.J., Cliby, W.A., Keeney G.L., Dodson M.K., Suman V.J., Roche P.C. and Podratz K.C. "Elevated nm23 Protein Expression is Correlated with Diminished Progression–Free Survival in Patients with Epithelial Ovarian Carcinoma". *Gynecologic Oncology* 1996 Mar.; 60(3): 363–372.

Sutherland, R.L. et al.; "Hormones and their Actions, Part 1", van der Molen, H.J., King, R.J.B. and Cooke, B.A. eds. *Elsevier Science Publishers B.V.*, Amsterdam, 1998 pp. 197–215.

Takao Ota, M.D. et al.; "Cystine Aminopeptidase and Leucine Aminopeptidase of Choriocarcinoma Cells Grown in Culture.", *American Journal of Obstertrics and Gynaecology* Jul. 15, 1975; 122(6):698–703.

Tsavaris N.B. et al.; "Correlation of Histoenzymological Studies with the Response to Chemotherapy and Survival in Breast Cancer Patients."; *Cancer Letters* Nov.; 1988 42(3):225–230.

* cited by examiner

I.

II.

TANDEM IMMUNO-ASSAY FOR CANCER

This application claims benefit of foreign priority from Canada patent 2,267,481, filed Mar. 30, 1999.

The present invention relates to the use of antibodies for the detection of cancer. More specifically, this invention relates to antibodies specific for NDP-kinase/Nm23 and estrogen stimulated Leucine Aminopeptidase (es-LAPase) and their use for the diagnosis of ductal carcinomas in situ (DCIS) and metastisis associated with breast cancer. The present invention also relates to a diagnostic system using an antibody to NDP-kinase together with an antibody specific for an estrogen simulated for es-LAPase to detect blood serum, plasma or tissue levels of the NDP-kinase and LAPase.

BACKGROUND OF THE INVENTION

The identification and characterization of risk factors and their molecular implications in the pathophysiology of human diseases such as breast cancer is essential for designing efficient diagnostic assays and therapeutic compounds. In particular, the accurate diagnostic of cancer type and aggressiveness (staging) is critical for the selection of the optimal therapeutic strategy. Staging relies on a combination of analysis including, but not limited to, histology of the tumour, detection of blood components and detection of cellular markers.

Diagnostic assays are available for breast cancer. For example, imaging techniques such as ultrasounds and x-rays (mammographies) are widely used to detect tumours. These imaging techniques, however, suffer from a limitation in the resolution of the image which prevents the detection of tumours below a certain size. Furthermore, fibroadenomas or cysts often share similar mammographic patterns as those found in malignant invasive tumours, making it difficult to determine tumour malignancy on the sole basis of mammography. Recent studies performed by Elmore (Lancet, 1999) and Goetze (Lancet, 2000) have clearly underlined the limitations of mammographic screening.

Histological analysis of biopsies is also a common procedure for the diagnosis of breast cancer and this technique relies on identification of visible phenotypes of the cells. However, this analysis is somewhat subjective and depends on the skill of the examiner.

Flow cytometry analysis of DNA from cells obtained from biopsies can also be analysed for DNA content as a measure of diploidy of cells, which may be correlated with the presence of cancer. However, such an analysis requires biopsies and extensive processing of the sample and access to costly instrumentation.

Amongst the various risk factors associated to the onset of early events leading to breast cancer, estrogen and estrogen-like compounds with estrogenic mimicking activity remain the most important determinants in the early events and progression of breast carcinogenesis. Under normal physiological conditions, there are several tissues whereby estrogenic steroids have been shown to play a critical function. These include the development of the reproductive tract, particularly secondary organs, such as the mammary glands. In addition, estrogens are also involved in the fine regulation of bone growth, liver and cardiovascular function and the estrus cycle, most likely through the induction of cell proliferation in target tissues [Sutherland, R. L., Watts, C. K. W., and Clarke, C. L. (1998). Hormones and Their Actions: Part 1 (van der Molen, H. J., King, R. J. B., Cooke, B. A., eds) pp. 197–215, Elsevier Science Publishing B. V., Amsterdam; Shekhar, P. V. M., Werdell, J., and Basrur, V. S. (1997). Environmental Estrogen Stimulation of Growth and Estrogen Receptor Function in Preneoplastic and Cancerous Human Breast Cell Lines. J. Natl. Cancer. Inst., 89: 1774–1782]. The response of such a variety of tissues to estrogen stimulation can explain in part its active role in the development and progression of different human carcinomas and in particular of breast cancer. Without wishing to be bound by any theory, it is thought that estrogens regulate various physiological functions by being involved in both "immediate-early" and "early" events of cell function. In this regard, it appears that immediate early events induced by estrogen lead to an increased cellular proliferation most likely through the reduction in the cell cycle by accelerating the rate at which cells progress from the $G_1$ phase towards the S phase. Recently, it has been proposed that estrogen promotes cellular proliferation by co-activating at similar estrogen concentrations, the expression of cyclin D1-Cdk4 and cyclin E-Cdk2, two critical and potentially interrelated $G_1$ regulatory peptides [Prall, O. W. J., Sarcevic, B., Musgrove, E. A., Watts, C. K. W. and Sutherland, R. L. (1997). Estrogen-induced Activation of Cdk4 and Cdk2 during $G_1$-S Phase Progression Is Accompanied by Increased Cyclin D1 Expression and Decreased Cyclin-dependent Kinase Inhibitor Association with Cyclin E-Cdk2. J. Biol. Chem., 272: 10882–10894].

Estrogen-based molecular diagnostics assays are available. The most widely used such assay measures estrogen and progesterone receptors in cells obtained from biopsies. It is particularly useful to determine whether a particular type of cancer will be responsive to hormonal therapy. However, this assay is of limited utility to evaluate the stage or progression of the disease and in particular it does not permit the detection of the presence of metastasis. This assay also suffers from the fact that it is necessary to obtain a biopsy. Apart from the fact that this constitutes an invasive procedure, it requires that the tumour be large enough to be detected by palpation or with imaging devices. Such large tumours may already be at a fairly advanced stage.

NDP-Kinase activity has been related to various physiological processes including DNA and RNA synthesis, production of cyclic AMP, superoxide metabolism and activation of the enzyme complex involved in DNA repair. In general the activity of NDP-Kinase has been parallelled to cellular proliferation, i.e. enhanced cytosolic NDP-Kinase activity is detected during cell proliferation. Moreover, the nm23 gene for which RNA levels are reduced in tumorous cells of high metastic potential, possesses a high degree of homology with the gene encoding the NDP-Kinase.

The nucleoside diphosphate-kinase facilitates the intracellular conversion of both deoxy and ribonucleotide diphosphates to their phosphorylated forms. Although the majority of the nucleoside diphosphate kinase (NDP-kinase) activity is found in the cytosol of various cell types, the enzyme is also present in other cell constituents such as the multimeric microtubule protein rings, isolated plasma membranes of human and rabbit platelets, and beef brain particulate material. The wide distribution of NDP-kinase reflects its active role in various fundamental cellular processes related to nucleotide and superoxide metabolism, synthesis of cyclic AMP and in general to cell proliferation and differentiation.

Its role in cell proliferation and differention makes NDP-kinase a candidate, as a cell marker, for cancer detection. This avenue has been explored by immuno-histochemical analysis of tissue sections from tumour biopsies. However, there was no clear correlation in these studies between the presence of NDP-kinase and the presence of cancerous cells

[Sawan A. et al., NDP-K/nm23 Expression in Human Breast Cancer in Relation to Relapse, Survival, and Other Prognostic Factors: an Immunohistochemical Study, Journal of Pathology January 1994; 172(1):27–34; Kobayashi S. et al., Estrogen Receptor, c-erbB-2 and nm23/NDP Kinase Expression in the Intraductal and Invasive Components of Human Breast Cancers, Japanese Journal of Cancer Research August 1992; 83(8):859–65; Srivatsa P. J. et al., Elevated nm23 Protein Expression is Correlated with Diminished Progression-Free Survival in Patients with Epithelial Ovarian Carcinoma, Gynecology Oncology March 1996; 60(3):363–72]

Other cellular markers have been studied for their correlation with cancer in general and breast cancer in particular. Among these markers serum LAPase has been found to correlate with invasiveness of breast cancer (Gupta S. K. et al., Serum Leucine Aminopeptidase Estimation: A Sensitive Prognostic Indicator of Invasiveness in Breast Carcinoma, Indian Journal of Pathology in Microbiology October 1989; 32(4):301–5]. However, variations in the level of serum LAPase is also associated with other types of cancer and other disease conditions such as systemic lupus erythematosus [Inokuma S. et al., Serum Leucine Aminopeptidase as an Activity Indicator in Systemic Lupus Erythematosus: A study of 46 Consecutive Cases, Rheumatology (Oxford) August 1999; 38(8):705–8], myocardial infarction [Gupta S. K. et al., Prognostic Significance of Serum Leucine Aminopeotidase in Myocardial Infarction with Left Ventricular Failure, Journal of Assoc. Physicians India November 1987; 35(11):760–2] and viral infections [Pancheva-haschen R. et al., Serum Leucine Aminopeptidase for Monitoring Viral Infections with Plasmacytoid Reaction, Enzyme 1986; 36(3):179–86] among others, making a diagnostic based on enzymatic assay of serum LAPase non specific. Without wishing to be bound by any theory, this non-specificity may be related to the presence of several isoenzymes of LAPase.

Clearly, there is a need for more rapid, more sensitive and less invasive methods for diagnosing and staging breast cancer. In particular, cellular markers, which reflect the presence of metastasis and markers indicative of estrogen activity are highly desirable.

The present invention provides for such a method. The method relies on monoclonal antibodies specific for NDP-Kinase and estrogen-stimulated LAPase capable of detecting these cellular markers in blood and tissues. Levels and enzymatic activity of these markers correlate with the aggressiveness in general and the presence of metastasis in patients with cancer and breast cancer in particular. This immuno-based assay may be done on blood samples or tissues from biopsies. A further advantage of the assay of the present invention is that by using two markers, the probability of false positives is greatly reduced. False positive could arise when using only one marker if blood levels of this marker are altered by other physiological conditions in the patient.

SUMMARY OF THE INVENTION

The present invention relates to the use of antibodies for the detection of cancer. More specifically, this invention relates to antibodies specific for NDP-kinase/Nm23 and estrogen stimulated Leucine Aminopeptidase (es-LAPase) and their use for the diagnosis of ductal carcinomas in situ (DCIS) and metastisis associated with breast cancer. The present invention also relates to a diagnostic system using an antibody to NDP-kinase together with an antibody specific for an estrogen simulated for es-LAPase to detect blood serum, plasma or tissue levels of the NDP-kinase and LAPase.

In one embodiment of the present invention there is provided a method of detecting breast cancer in a patient by determining the level of NDP-kinase and es-LAPase in a sample.

Also according to the present invention there is provided a method of detecting a metastatic cancer in a patient by determining the level of NDP-kinase and es-LAPase in a sample.

The present invention also relates to a diagnostic system using an antibody to NDP-kinase together with an antibody specific for an estrogen simulated LAPase to detect blood serum, plasma or tissue levels of the NDP-kinase and es-LAPase.

BRIEF DESCRIPTION OF THE DRAWINGS

These and other features of the invention will become more apparent from the following description in which reference is made to the appended drawings wherein.

DESCRIPTION OF PREFERRED EMBODIMENT

Figure 1:
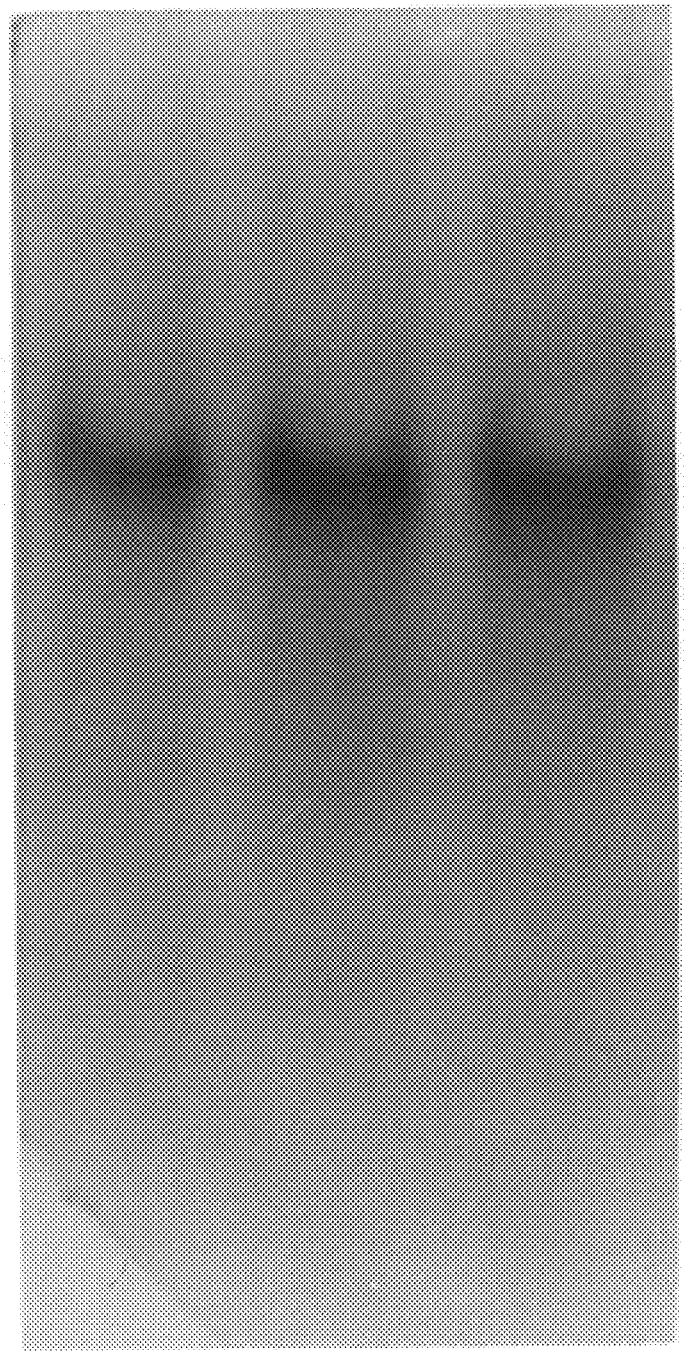
FIG. 1 shows the reactivity of MAb 4A12 in Western blots of non-denatured NDP-Kinase/Nm23 containing samples. After non-denaturing PAGE, crude cytosolic (lane 1), pure preparation of NDP-kinase/Nm23 from HL 60 cells (lane 2) and recombinant Nm23-H1 (lane 3) were reacted with Mab 4A12. In all samples the same protein component with identical electrophoretic mobility was recognized by Mab 4A12.

The present invention relates to the use of antibodies for the detection of cancer. More specifically, this invention relates to antibodies specific for NDP-kinase/Nm23 and estrogen stimulated Leucine Aminopeptidase (es-LAPase) and their use for the diagnosis of ductal carcinomas in situ (DCIS) and metastasis associated with breast cancer. The present invention further relates to a diagnostic system comprising an antibody specific for NDP-kinase/Nm23 to detect blood serum, plasma or tissue levels of the NDP-kinase together with an antibody specific for an estrogen simulated LAPase to detect blood serum, plasma or tissue levels of the NDP-kinase and LAPase.

In early studies [Cheng et al, Biochemistry 12:5 (1973)] it was suggested that the NDP-kinase might exist as various isoenzymes with characteristic isoelectric points and molecular weights. By contrast, studies (enzyme kinetics, peptide mapping and immunoblotting) performed on both the membrane-associated and cytosolic NDP-kinase [Kimura et al, J Biol Chem 263:4647 (1988)], have shown that both enzymes are identical monoisozymic forms of the NDP-kinase. The inventors have found that the active cytosolic NDP-kinase purified from HL60 cells is an oligomer of about 67 kDa composed of two distinct subunits of approximately 17 kDa and 33 kDa respectively, and that the cytosolic NDP-kinase is monoisozymic and the various apparent isozymes are the result of different states of phosphorylation of the protein, and not the product of NDP-kinase proteolysis.

In accordance with the present invention, we have prepared monoclonal antibodies against purified cytosolic NDP-kinase from HL60 cells. One of the monoclonal antibodies (MAb4A12) can selectively react with the active oligomer of the NDP-kinase. After denaturation, the monomeric components of this enzyme are no longer recognized therefore, native NDP-kinase conformation is required for binding of the MAb4A12 antibody. NDP-kinase has been found in both the cytoplasm and as a membrane associated complex. Furthermore, identical kinetic and physiochemical properties have been reported for NDP-kinase in both sites.

Further according to the present invention there is provided an antibody specific for an estrogen or estrogen analog stimulated leucine aminopeptidase (es-LAPase). The preparation of this antibody is described in detail in Applicant's copending patent application entitled "A Monoclonal Antibody Against Estrogen Stimulated Leucine Aminopeptidase", and which is incorporated herein by reference.

The monoclonal antibody of the present invention was prepared by conventional procedures, generally following the methods of Campbell (1984, In: Laboratory techniques in biochemistry and molecular biology (Burdon, R. H., Knippenberg P. H. V., eds) Amsterdam, Elsevier: 219–223) and Lietzke, R. and Unsicker, K (J. Immunol. Methods 76:223–228, 1985). According to this method, tissue culture adapted mouse myeloma cells are fused to antibody producing cells from immunized mice to obtain hybrid cells that produce large amounts of a single antibody molecule. In general, the antibody producing cells are prepared by immunizing an animal, for example, mouse, rat, rabbit, sheep, horse, or bovine, with an antigen. The immunization schedule and the concentration of the antigen in suspension is such as to provide useful quantities of suitably primed antibody producing cells. These antibody producing cells can be either spleen cells, thymocytes, lymph node cells and/or peripheral blood lymphocytes.

The antibody producing cells are then fused with myeloma cells, cell lines originating from various animals such as mice, rats, rabbits, and humans can be used, using a suitable fission promoter. Many mouse myeloma cell lines are known and available generally from members of the academic community and various depositories, such as the American Type Culture Collection, Manassas, Virginia. The myeloma cell line used should preferably be medium sensitive so that unfused myeloma cells will not survive in a selective media, while hybrids will survive. The cell line most commonly used is an 8-azaguanine resistant cell line, which lacks the enzyme hypoxanthine-guanine-phosphoribosyl-transferase and therefore will not be supported by HAT (hypoxanthine-aminopterin-thymidine) medium. In general, the cell line is also preferably a "non-secretor" type, in that it does not produce any antibody. The preferred fusion promoter is polyethyleneglycol having an average molecular weight from about 1000 to about 4000. Other fusion promoters such as polyvinylalcohol, a virus or an electrical field can also be used.

The immortalized cells (hybridoma) must then be screened for those which secrete antibody of the correct specificity. The initial screening is generally carried out using an enzyme-linked immunosorbent assay (ELISA). Specifically, the hybridoma culture supernatants are added to microtitre plates or nitrocellulose membranes which have been previously coated with the antigen, in this case NDP-kinase/Nm23 purified from HL60 cells. A bound specific antibody from the culture supernatants can be detected using a labelled second antibody, for example, goat antimouse IgG labelled with peroxidase, which is commercially available. Cultures that are positive against the NDP-kinase antigen are then subjected to cloning by the limiting dilution method. Secondary hybridoma cultures are then re-screened as described above. The cultures are then evaluated as to determine whether or not the antibody binds the antigen and to determine the kinetic profile of antigen binding. Selected cultures based on these results are subject to further cloning until culture stability and clonality are obtained. Immediately after hybridization, the fusion products will have approximately 80 chromosomes, and as these cells proceed to divide they will randomly lose some of these chromosomes. The cloning process is to select those cells which still have the chromosomes coding for antibody production. The cloning process is repeated until 100% of the sub-population exhibits the production of a specific antibody, which is indicative of the "stability" of the hybridoma. In addition, hybridoma culture wells often have multiple colonies some of which may be antibody non-producers. The cloning process allows the selection of a positive hybrid which is derived from a single cell.

In one example of the present invention, a hybridoma cell line 4A12, producing the monoclonal antibody 4A12, was prepared. This monoclonal antibody is specific for NDP-kinase/Nm23. This hydridoma cell line was deposited in the American Type Culture Collection on May 27, 1994 and has been awarded serial number CRL 11634.

The 4A12 antibody is of the IgG2a subtype and recognizes the membrane as well as the cytosolic form of NDP-kinase/nm23. The antibody displays a detectable binding to many cell types, including cells of the hemapoietic lineage. However, the antibody is specific for B lymphocyte and does not recognize other lymphocytes. In this respect, breast cancer patients with metastatic disease exhibit a marked decrease in NDP-kinase positive B cells. It will therefore be recognized that the antibody of the present invention is very useful in the diagnostic of metastatic disease in such patients.

In one example of the present invention, a hybridoma cell line 7B6, producing the monoclonal antibody 7B6, was prepared. This monoclonal antibody is specific for estrogen stimulated LAPase. This hybridoma cell line was deposited with the International Depositary Authority of Canada, Room 5190, 1015 Arlington Street, Winnipeg, Manitoba, Canada, R3E 3R2, on Mar. 23, 2000 under Accession Number IDAC 230300-1.

The hybridoma cell lines described in the present application have been deposited in accordance with 37 C.F.R. §1.808. Furthermore, subject to paragraph (b) of 37 C.F.R. §1.808, all restrictions imposed by the depositor on the availability to the public of the deposited material will be irrevocably removed upon the granting of any patent issuing from this application or from any continuing application based thereon.

The present invention also encompasses the antibodies of the present invention and any fragments thereof containing the active binding region of the antibodies such as Fab, $F(ab)_2$ and Fv fragments. These fragments can be obtained from the 7B6 or 4A12 antibody by using techniques well known to those of skills in the art (Rousseaux et al. Methods Enzymology, 121:663–69, Academic Press, 1986).

A further embodiment of the present invention encompasses antibodies or fragments thereof capable of binding the same antigenic determinant as the 7B6 or 4A12 antibody. Including, but not limited to, antibodies possessing the same antigenic specificity as the 7B6 or 4A12 antibody but originating from a different species or having a different isotype or exhibiting different binding affinities. It is envisioned that class and isotype variants of the antibody of the present invention can be prepared using recombinant class switching and fusion techniques that are well known to those skilled in the art (see for example: Thammana et al. Eur. J. Immunol, 13:614, 1983; Oi et al., Biotechnologies, 4(3):214–221, Liu et al. Proc. Nat. Acad. Sci. (USA), 84:3439–43, 1987; Neuberger et al., Nature 312:604–608, 1984 and Spira et al. J. Immunol. Meth., 74:307–15, 1984).

The monoclonal antibodies of the present invention can be produced either using a bioreactor or from ascites, both procedures of which are well known in the art.

The monoclonal antibodies of the present invention can be used for diagnostic applications for the detection of metastasis and staging of disease in breast cancer and other types of cancers such as brain cancer of glial origin using immunoassay systems for determining the levels of NDP-kinase/nm23 together with the levels of es-LAPase. in blood and tissues.

In one aspect of the present invention, immunoprecipates using MAb 4A12 of cell fractions from parental epithelial like cells isolated from tumour biopsies of women with breast carcinomas indicates that NDP-Kinase activity is reduced in the stromal fraction and increased in the cytopholic fractions. Furthermore, immunoprecipates of plasma using MAb 4A12 also indicates an increase in NDP-Kinase/nm23 levels in women with ductal carcinomas in situ (DCIS) and metastatic disease.

In a further aspect of the present invention, Mab 4A12 of the present invention can be used to detect cells exhibiting surface or membrane associated NDP-Kinase/nm23. In particular, the reactivity and distribution of Mab 4A12 in human peripheral blood cells has been analyzed. It has been found that both monocytes and granulocytes react with MAb 4A12, but that only a fraction of lymphocytes react with the antibody. Further analysis have demonstrated that only B lymphocytes and more specifically CD19+ lymphocytes react with anti-NDP-Kinase/nm23 antibody of the present invention. In this aspect of the invention, it is provided that the detection of the antigen recognized by MAb 4A12 on CD19+B cells of patients with breast cancer and on brain tumour cells of glial origin, has been inversely correlated with the presence of metastasis and increase tumour aggressiveness. In addition, the present invention uses MAb7B6 together with MAb 4A12 to detect cells exhibiting surface or membrane associated NDP-Kinase/nm23 and es-LAPase.

Immunoassays involve contacting a sample such as tissue or blood with the antibodies of the present invention and detecting the presence of antibody-antigen adduct. Also, the sample can be immunoprecipitated and the levels or activity of the enzyme in the immonoprecipitate can be measured.

Certain immunoassays utilize a double antibody method for detecting the presence of an antigen. These techniques are reviewed in "Basic Principals of Antigen-Antibody Reaction", Elvin A. Labat, (Methods in Enzymology, 70, 3–70, 1980). Such systems are often referred to as fast format systems because they are adapted to rapid determinations of the presence of an antigen. The system requires high affinity between the antibody and the antigen.

According to one embodiment of the present invention, the presence of NDP-kinase/nm23 is determined using a pair of antibodies, each specific for NDP-kinase/nm23. One of said pairs of antibodies is referred to herein as a "detector antibody" and the other of said pair of antibodies is referred to herein as a "capture antibody". The monoclonal antibodies of the present invention can be used as either a capture antibody or a detector antibody. The monoclonal antibodies of the present invention can also be used as both capture and detector antibody, together in a single assay. One embodiment of the present invention thus uses the double antibody sandwich method for detecting NDP-kinase in a sample of biological fluid. In this method, the antigen is sandwiched between the detector antibody and the capture antibody, the capture antibody being irreversibly immobilized onto a solid support. The detector antibody would contain a detectable label, in order to identify the presence of the antibody-antigen sandwich and thus the presence of the antigen. In one aspect of the present invention each marker, NDP-kinase and es-LAPase are assayed in a single system, using an antibody specific for each marker, with the double antibody sandwich method, described above.

Common early forms of solid supports were plates, tubes or beads of polystyrene which are well known in the field of radioimmunoassay and enzyme immunoassay. More recently, a number of porous materials such as nylon, nitrocellulose, cellulose acetate, glass fibers and other porous polymers have been employed as solid supports.

One embodiment of the present invention uses a flow-through type immunoassay device. Valkirs et al. (U.S. Pat. No. 4,632,901) discloses a device comprising antibody, specific to an antigen analyte, bound to a porous membrane or filter to which is added a liquid sample. As the liquid flows through the membrane, target analytes bind to the antibody. The addition of the sample is followed by the addition of a labelled antibody. The visual detection of the labelled antibody provides an indication of the presence of the target analyte in the sample.

Another example of a flow-through device is disclosed in Kroner et al. (EP-A 0 229 359), which described a reagent delivery system comprising a matrix saturated with a reagent or components thereof dispersed in a water soluble polymer for controlling the dissolution rate of the reagent for delivery to a reaction matrix positioned below the matrix.

In migration type assays, a membrane is impregnated with the reagents needed to perform the assay. An analyte detection zone is provided in which labelled analyte is bound and assay indicia is read. For example, see Tom et al. (U.S. Pat. No. 4,366,241), and Zuk (EP-A-143 574). Migration assay devices usually incorporate within them reagents which have been attached to colored labels thereby permitting visible detection of the assay results without addition of further substances. See for example Bernstein (U.S. Pat. No.

4,770,853), May et al. (WO 88/08534), and Ching et al. (EP-A 0 299 428). The monoclonal antibody of the present invention can be used in all of these known types of flow-through devices. These flow-through devices can also be used when more than one single analyte is to be detected in a single sample. Thus, according to one embodiment of the present invention these flow through devices can be used for the detection of estrogen stimulated leucine aminopeptidase and cytosolic NDP-kinase/Nm23.

Direct labels are one example of labels which can be used according to the present invention. A direct label has been defined as an entity, which in its natural state, is readily visible, either to the naked eye, or with the aid of an optical filter and/or applied stimulation, e.g. U.V. light to promote fluorescence. Among examples of coloured labels, which can be used according to the present invention, include metallic sol particles, for example, gold sol particles such as those described by Leuvering (U.S. Pat. No. 4,313,734); dye sol particles such as described by Gribnau et al. (U.S. Pat. No. 4,373,932) and May et al. (WO 88/08534); dyed latex such as described by May, supra, Snyder (EP-A 0 280 559 and 0 281 327); or dyes encapsulated in liposomes as described by Campbell et al. (U. S. Pat. No. 4,703,017). Other direct labels include a radionucleotide, a fluorescent moiety or a luminescent moiety. In addition to these direct labelling devices, indirect labels comprising enzymes can also be used according to the present invention. Various types of enzyme linked immunoassays are well known in the art, for example, alkaline phosphatase and horseradish peroxidase, lysozyme, glucose-6-phosphate dehydrogenase, lactate dehydrogenase, urease, these and others have been discussed in detail by Eva Engvall in Enzyme Immunoassay ELISA and EMIT in *Methods in Enzymology*, 70. 419–439, 1980 and in U.S. Pat. No. 4,857,453.

Other examples of biological diagnostic devices, which can be used for the detection of NDP-kinase/nm23 and es-LAPase, using the monoclonal antibodies of the present invention, include the devices described by G. Grenner, P.B. Diagnostics Systems, Inc., in U.S. Pat. Nos. 4,906,439 and 4,918,025.

In one embodiment of the present invention, the diagnostic test uses a blood sample tube which is commonly used to draw blood samples from patients. The inside wall of the tube acts as a carrier for the monoclonal or polyclonal antibodies and required reagents or detection means, needed to produce a measurable signal. In this embodiment the capture antibody is immobilized onto the wall of the test tube. After the sample is drawn from the patient, the user simply shakes the sample with the detector antibody in the tube so that the detector antibody reacts with any NDP-kinase/Nm23 or es-LAPase in the blood. In this example the monoclonal antibodies of the present invention can be either the capture antibody or the detector antibody. It may be necessary to use a sample wherein the red blood cells have been removed, so that the red blood cells will not interfere with the analysis of the results. If the analyte is present in the blood, it will be sandwiched between the capture antibody and the detector antibody which contains a suitable label for direct detection or reacts with the reagents in an indirect assay. The solid support (the test tube) can then be rinsed free of unbound labelled material. A variety of solid supports can be used according to this method, for example, test tube walls, plastic cups, beads, plastic balls and cylinders including microtitre plates, paper, and glass fibres.

There are currently available several types of automated assay apparatus which can undertake rapid format assays on a number of samples contemporaneously. These automated assay apparatus include continuous/random access assay apparatus. Examples of such systems include OPUS™ of PB Diagnostic System, Inc. and the IMX™ Analyzer introduced by Abbott Laboratories of North Chicago, Ill. in 1988. In general, a sample of the test fluid is typically provided in a sample cup and all the process steps including pipetting of the sample into the assay test element, incubation and reading of the signal obtained are carried out automatically. The automated assay systems generally include a series of work stations each of which performs one of the steps in the test procedure. The assay element may be transported from one work station to the next by various means such as a carousel or movable rack to enable the test steps to be accomplished sequentially. The assay elements may also include reservoirs for storing reagents, mixing fluids, diluting samples, etc. The assay elements also include an opening to permit administration of a predetermined amount of a sample fluid, and if necessary, any other required reagent to a porous member. The sample element may also include a window to allow a signal obtained as a result of the process steps, typically a fluorescent or a calorimetric change in the reagents present on the porous member to be read, such as by a means of a spectroscopy or fluorometer which are included within the assay system.

The automated assay instruments of PB Diagnostic Systems, Inc. are described in U.S. Pat. Nos. 5,051,237; 5,138,868; 5,141,871 and 5,147,609.

A description of the IMX™ Analyzer is included in the "Abbott IMX Automated Bench Top Immunochemistry Analyzer System" by Fiore, M. et al., *Clinical Chemistry*, 35, No. 9, September 1988. A further example of these analyzers has been described in U.S. Pat. No. 4,956,148 entitled "Locking Rack and Disposable Sample Cartridge" issued to C. J. Grandone on Sep. 1, 1990, and assigned to Abbott Laboratories, which describes a carousel for carrying a plurality of reaction cells for use in connection with the Abbott IMX™ system. A further development in the art has been described in Canadian Patent Application 2,069,531, Chadwick M. Dunn et al., assigned to Abbott Laboratories wherein the immunochemistry analyzer system, described in this prior art application, has the capability of testing for up to three or four analytes in a single batch during a single run using currently available instrumentation. The system described in the Canadian application referred to above enables the users to group three small batches of assays together rather than run three separate analysis. The monoclonal antibody of the present invention can be used in these automated analyzers.

A further class of immunochemical analyzer systems, in which the monoclonal antibodies of the present invention can be used, are the biosensors or optical immunosensor systems. In general an optical biosensor is a device which uses optical principles quantitatively to convert chemical or biochemical concentrations or activities of interest into electrical signals. These systems can be grouped into four major categories: reflection techniques; surface plasmon resonance; fibre optic techniques and integrated optic devices. Reflection techniques include ellipsometry, multiple integral reflection spectroscopy, and fluorescent capillary fill devices. Fibre-optic techniques include evanescent field fluorescence, optical fibre capillary tube, and fibre optic fluorescence sensors. Integrated optic devices include planer evanescent field fluorescence, input grading coupler immunosensor, Mach-Zehnder interferometer, Hartman interferometer and difference interfermoter sensors. These examples of optical immunosensors are described in general in a review article by G. A. Robins (Advances in Biosensors), Vol.1, pp.229–256,1991. More specific description of these devices are found for example in U.S. Pat. Nos. 4,810,658; 4,978,503; 5,186,897; R. A. Brady et al. (Phil. Trans. R. Soc. Land. B 316, 143–160, 1987) and G. A. Robinson et al. (in Sensors and Actuators, Elsevier, 1992).

Another immunochemical method of analysis is flow cytometry. In flow cytometry the sample containing the antigen is reacted with a fluorescently labelled form of the monoclonal antibody of the present invention. The sample is passed in front of a laser beam of a given wavelength capable of exciting the chromophore on the antibody. Each particle or cell having the antibody bound to it will fluoresce and will be detected. This technique allows the analysis of specific cell types and in particular of specific blood cell types. It is therefore useful for the detection of B cell exhibiting the NDP-kinase/Nm23 or es-LAPase antigens.

NDP-kinase and LAPase activities can also be determined using plasma immunoprecipitates obtained by immunoprecipitation using covalent Mab 4A12 and Mab 7B6 each bound to a solid support. Briefly, plasma, or a dilution of the plasma was added to the covalently bound MAbs and incubated for a sufficient time to ensure that any marker in the sample was bound to the monoclonal antibodies. Individual enzyme activities can then be determined.

In one embodiment of the present invention, the analytes are detected in a sample of blood, serum, plasma or tissues using the monoclonal antibody of the present invention, in a device comprising a filter membrane or solid support with a detection section and a capture section. The detector section contains an antibody (a detector antibody), which will react with NDP-kinase/Nm23. The detector antibody is reversibly immobilized onto the solid support and will migrate with the sample, when in use. It is preferred that the detector antibody is labelled, for example with a radionucleotide, an enzyme, a fluorescent moiety, luminescent moiety or a coloured label such as those described in the prior art, and discussed above. The capture section comprises a capture antibody, which is irreversibly immobilized onto the solid support. The antibodies, capture and detector antibody, and the necessary reagents are immobilized onto the solid support using standard art recognized techniques, as disclosed in the flow-through type immunoassay devices discussed previously. In general, the antibodies are absorbed onto the solid supports as a result of hydrophobic interactions between non-polar protein substructures and non-polar support matrix material.

In a further embodiment of the of the present invention, the antibody which will react with NDP-kinase/Nm23 can be used, in a tandem assay, in conjunction with another antibody, more specifically the antibody specific for the human es-LAPase. Serum LAPase is more elevated in patients with breast cancer and still more elevated in breast cancer patients with metastatic disease (see example infra). Furthermore, es-LAPase is more elevated in supernatant of breast carcinoma cell cultures that have been exposed to estrogens. Thus in the tandem assay, both antibodies are used simultaneously to detect NDP-kinase/nm23 and serum es-LAPase levels in blood samples. The tandem assay overcome limitations of the prior art in that it uses two markers that are both sensitive to the presence of metastasis in patients with breast cancer. Therefore, the specificity and accuracy of the assay for breast cancer is increased by lowering the probability of false positives.

In a further embodiment of this invention the tandem assay can also be used to monitor patients that are at risk of developing breast cancer. In particular, since both serum es-LAPase and NDP-kinase/nm23 are affected by estrogens, individuals at risk may include those taking estrogen based birth control pills, hormonal replacement therapy or individuals having abnormal hormonal patterns. Thus, according to this aspect of the present invention, if a woman is being treated with therapeutic estrogen, her levels of these two markers in her serum can be monitored to determine if the level of NDP-kinase and es-LAPase increases. Thus, as increased levels of NDP-kinase and es-LAPase correlate with an increase risk of developing breast cancer, such women could reduce their risk by reducing their estrogen intake.

As would be recognized by one of skill in the art, a base line level of NDP-kinase/Nm23 and es-LAPase may be present in normal patients. Thus, in the present invention, in certain embodiments, the levels of NDP-kinase/Nm23 and es-LAPase above normal will be determined. This can be accomplished by either comparing the results to the results of a normal patient, or adjusting the sensitivity of the immunoassay so that only values above a certain threshold will show as a positive result.

As would be recognized by one of skill in the art, the above described embodiments of this invention may have to be modified to distinguish between the cytosolic and membrane associated NDP-kinase/Nm23.

In order that the invention described herein may be more fully understood, the following examples are set forth. It should be understood that these examples are for illustrative purposes only and are not to be construed as limiting the scope of this invention in any manner.

EXAMPLES

Example 1

Isolation and Purification of Cytosolic NDP-Kinase from HL60 Cells

Cytosolic NDP-Kinase from HL60 cells was purified as described by Pulido-Cejudo et al [FASEB J 3:608a (1989)]. Briefly, the cytosolic fraction of cell extracts obtained from 15 grams (wet weight) of phosphate-buffered saline (PBS) washed HL60 cell pellets were applied to a phosphate cellulose column (P11) (1.6 cm×28.0 cm) previously equilibrated in phosphate buffer A [50 mM potassium phosphate pH 7.0, 2 mM $MgCl_2$, 1 mM PMSF, 1 mM DTT and 10% glycerol]. The column was washed with 300 ml of the same buffer at a flow rate of 0.1 ml/min. Unbound protein was concentrated to 10 ml by ultrafiltration using YM5 membrane (5000 M.W. cutoff, Amicon Div., Danvers, Mass., USA). The concentrate was applied to a DEAE cellulose column (2.6 cm×28.5 cm) equilibrated and washed with Tris buffer [50 mM Tris-HCl pH 7.5; 2 mM $MgCl_2$; 1 mM PMSF; 1 mM DTT and 10% (v/v) glycerol]. NDP-Kinase/Nm23 was eluted using a linear gradient (0 to 1M NaCl in Tris buffer) at a flow rate of 0.50 ml/min. Determination of the activity of the purified material containing NDP-Kinase/Nm23 was determined as described by G. Pulido-Cejudo et al [J. Chromatogr. B 660 (1994) 37–47)]. Briefly, NDP-Kinase/Nm23 activity was determined by measuring the amount of dATP consumed with dADP as phosphate acceptor and a fixed amount of enzyme. DEAE ion exchange paper (DE81) was used to separate $^3$HdATP from the remaining $^3$HdADP after NDP-Kinase/Nm23 mediated phosphate transfer to unlabelled dADP. Before use, all deoxynucleotides and ribonucleotides were purified by anion exchange chromatography. 23 mM solutions of each nucleotide were loaded onto a Partisil 10SAX analytical column equilibrated with 0.4 M $NH_4H_2PO_4$, pH 3.9. Isocratic elution of the two samples was 1700 to 1800 psi (Waters HPLC system Model 510). The pH of the purified material was adjusted to 7.0 with ammonia, and the final concentration determined spectrophotometrically at 260 nm. Fractions containing NDP-Kinase/Nm23 activity were pooled and subsequently concentrated by ultrafiltration. NDP-Kinase/Nm23 concentrate was loaded into a Sephacryl S-200 column (2.6 cm×51 cm) pre-equilibrated in Tris buffer and the active material recovered after this purification step. Protein concentration following each purification step was determined as described by Pulido-Cejudo [J. Chromatogr. B 660 (1994) 37–47)]. Briefly, samples (100–200 $\mu$l) were dialysed against deionized water and 2–20 $\mu$l of each were placed in polypropylene tubes. Samples were dried for 60 min at 110° C. for 90 min and subsequently neutralized with 250 $\mu$l of glacial acetic acid. The samples were then reacted with 500 $\mu$l of the following ninhydrin-hydrindantin solution: 2 g of ninhydrin and 150 mg of hydrindatin (Sigma) were dissolved in 65 ml of 2-methoxyethanol and then 35 ml of 4 M sodium acetate (pH 5.5) were added. The tubes were incubated at 110° C. for 15 min. Before reading the absorbance of the samples at 570 nm, 2.5 ml of 5% (v/v) ethanol were added. Protein content was determined by interpolation on an absorbance curve obtained with samples of BSA (1–10 $\mu$g). A summary of the purification of the cytosolic NDP-Kinase/Nm23 from HL60 cells is set out in Table 1.

TABLE 1

Summary of Purification of the NDP-Kinase from HL60 Cells

| Step | Protein[1] (mg) | Total Activity[2] (nmole/min) | Specific Activity[2] (nmole/min) | Fold | Yield % |
|---|---|---|---|---|---|
| Homogenate | 875 | 125 | 0.14 | 1 | 100 |
| Supernatant | 623 | 102 | 0.16 | 1.15 | 81.60 |
| Cellulose | | | | | |
| Phosphate | 135 | 100 | 0.74 | 5.21 | 80.00 |
| Cellulose | | | | | |
| DEAE | 1.18 | 14 | 11.86 | 83.52 | 11.20 |
| Sephacryl S-200 | 0.006 | 6 | 1000 | 7042 | 4.80 |

[1]the amount of protein was determined after alkaline hydrolysis and quantitative ninhydrin detection of hydrolysed material.
[2]determined with a first-order assay (Pulido-Cejudo et al. J. Chromatogr. B. 660, 37–47.

Example 2

Isolation and Purification of Estroge-Stimulated Leucine Aminopeptidase (es-LAPase)

Primary parental breast carcinoma cells obtained from human tumour biopsies were stimulated with 100 nM 17-β-Estradiol for 24 hours or cell media alone as a control. The cell media was RPMI 1640 medium +10% FCS +100 U/ml Penicillin +100 $\mu$g/ml Streptomycin. Cell supernatants were collected then after and dialyzed against PBS in seamless cellulose tubing (MW 12,400) for 12 hours at 4° C. LAP was subsequently purified from the dialyzed cell supernatants using HPLC-gel permeation followed by DEAE-Cellulose and Bestatin-Sepharose affinity Chromatography. Briefly, the cell supernatant was applied to a Bio-Sil SEC-250 column (600×7.5 mm) previously equilibrated in a buffer containing 100 mM Sodium Phosphate buffer pH 6.8, 100 mM $Na_2SO_4$, 1 $\mu$M $ZnCl_2$ and 10% glycerol. The column was washed with 300 ml of the same buffer at a flow rate of 0.5 ml/min. Protein was concentrated to 10 ml by ultrafiltration using YM5 membrane (5000 M.W. cutoff, Amicon Div., Danvers, Mass., USA). The concentrate was applied to a DEAE cellulose column (2.6 cm×28.5 cm) equilibrated and washed with 50 mM Tris-HCl buffer pH 7.5; 1 $\mu$M $ZnCl_2$; and 10% (v/v) glycerol. LAP was eluted using a linear gradient (0 to 1M NaCl in Tris buffer) at a flow rate of 0.50 ml/min. A Bestatin-affinity column was prepared using Ultralink EDC/DADPA Amide bonding matrix (Pierce, Rockford, Ill. U.S.A.) by reacting 100 mg of pure Bestatin with the carbodiimide EDC/DADPA matrix following the procedure provided by the manufacturer. Prior to loading the LAP containing eluent, the Bestatin-affinity column was equilibrated with 10 mM Tris-HCl pH 8.0 containing 1 $\mu$M $ZnCl_2$ and washed with 300 ml of this binding buffer. LAPase was recirculated through the system using a peristaltic pump at a flow rate of 0.10 ml/min, for 2 hours. Following this recirculation, the column was washed with eight column volumes of binding buffer. Bestatin-bound LAPase was eluted with a linear gradient (0–0.5 M NaCl) prepared in binding buffer 10 mM Tris-HCl pH 8.0 containing 1 $\mu$M $ZnCl_2$. Elution of bound LAP was monitored by absorbance at 280 nm. Purified LAPase fractions were aliquoted in 500 $\mu$l and stored until further use in 50 mM Tris-HCl pH 7.8 and 50 $\mu$M $ZnCl_2$. LAPase protein concentration following each purification step was determined as described by Pulido-Cejudo [J. Chromatogr. B 660 (1994) 37–47)]. Briefly, samples (100–200 $\mu$l) were dialysed against deionized water and 2–20 $\mu$l of each were placed in polypropylene tubes. Samples were dried for 60 min at 110° C. for 90 min and subsequently neutralized with 250 $\mu$l of glacial acetic acid. The samples were then reacted with 500 $\mu$l of the following ninhydrin-hydrindantin solution: 2 g of ninhydrin and 150 mg of hydrindantin (Sigma) were dissolved in 65 ml of 2-methoxyethanol and then 35 ml of 4 M sodium acetate (pH 5.5) were added. The tubes were incubated at 110° C. for 15 min. Before reading the absorbance of the samples at 570 nm, 2.5 ml of 5% (v/v) ethanol were added. Protein content was determined by interpolation on an absorbance curve obtained with samples of BSA (1–10 $\mu$g).

Example 3

Production and Purification of Monoclonal Antibodies MAb 7B6 (Anti-LAPase) & MAb 4A12 (Anti-NDP-kinase)

The protocols for antigen preparation for immunization, preparation of spleen cells from immune animals, fusion of spleen cells with myeloma cells and plating of fused cells in selective HAT medium was conducted following the detailed guidelines described by Campbell [Burdon RH, Knippenberg PHV (eds): Laboratory Techniques in Biochemistry and Molecular Biology, Amsterdam, Elsevier, p219 (1984)] and by Lietzke and Unsicker [Lietzke R. Unsicker K: A Statistical Approach to Determine Monoclonality After Limiting Cell Plating of a Hybridoma Clone, J Immunol Methods 76:223 (1985)]. Contrary to most standard procedures used for the production of monoclonal antibodies, the primary immunization was performed with highly purified NDP-kinase (7000 purification fold—see Table 1) and not with crude or partially purified enzyme preparations. The production of ascitic fluid was achieved by priming BALB/C mice with 500 1 of pristane one week before intraperitoneal injection of $3\times10^6$ hybridoma cells. Ascitic fluid was collected after 20 days by draining the peritoneal cavity. Purification of IgG immunoglobulins from ascitic fluids was performed by affinity chromatography on a 3 ml Protein G Sepharose 4 FF column (Pharmacia, Uppsala Sweden) following the manufacturer's protocol.

Screening of monoclonal antibodies against NDP-Kinase was performed by dot blot immunostaining on nitrocellulose. Briefly, 0.5 to 1 μg of NDP-kinase (5 μl) was spotted onto a nitrocellulose membrane dried and blocked for one hour at 37° C. with PBS/3% BSA (blocking solution). The mouse monoclonal antibodies (1/100 and 1/500 dilutions) were prepared in blocking solution and reacted with immobilized NDP-kinase at 37° C. for 17 hours and then detected using an immunoperoxidase method.

One monoclonal antibody Mab 4A12, was deposited with the American Type Culture Collection on May 27, 1994, under Accession Number CRL 11634.

In producing the hybridoma cell line 7B6 secreting the mouse monoclonal antibody to 17-β-Estradiol-respondant LAPase, protocols for antigen preparation for immunization, preparation of spleen cells from immune animals, fusion of spleen cells with myeloma cells and plating of fused cells in selective medium was conducted following detailed guidelines described by Campbell [Burdon RH, Knippenberg PHV (eds): Laboratory Techniques in Biochemistry and Molecular Biology, Amsterdam, Elsevier, p219 (1984)] and by Lietzke and Unsicker [Leitzke R. Unsicker K: A Statistical Approach to Determine Monoclonality After Limiting Cell Plating of a Hybridoma Clone, J Immunol Methods 76:223 (1985)].

Briefly, the primary immunization was performed with purified es-LAPase following desalting. Boosts with purified es-LAPase were performed at days 14, 35 & 56. BALB/c mice were screened at days 24 & 45. The mice were sacrificed at day 59 and the splenocytes from the best responder were fused with myeloma cells. Screening was performed by dot blot immunostaining on nitrocellulose.

The hybridoma clone 7B6 was obtained by single cell cloning by limiting dilution. Four dilution tubes in series containing hybridoma cells with medium supplement with 20% FBS+2×OPI were prepared. 100 μl of each dilution was plated in a 96-well plate with 50 μl of splenocyte feeder cells in each well and placed inside a 37° C. 5% $CO_2$ incubator. At day 7, supernatants from each well were removed and screened by dot blot immunostaining on nitrocellulose.

Hybridoma clone 7B6 cells were transferred from the 96 well plate to 0.5 ml medium supplemented with 20% FBS+ 1×OPI+1×HAT in a 24 well plate. Once the cells were dense, they were transferred into 5 mls in a 60 mm dish and then transferred to 10 mls in a 100 mm dish. Once in the 60 mm dish, the cells were weened off hypoxanthine, thymidine and aminopterin. 7B6 hybridoma cells were continued to be grown until in a log phase of growth. Anti-LAPase, Mab 7B6 was isolated from collected hybridoma 7B6 cell supernatant by affinity chromatography using Immunopure IgG as per described by manufacturer. Screening was performed by dot blot immunostaining on nitrocellulose.

The isotypes of Mab 4A12 and that of Mab 7B6 were determined using Sigma's immunotype Kit. Briefly, the assay involves binding of the monoclonals to a precoated isotyping nitrocellulose membrane strip followed by immunodetection using a sensitive biotin-avidin-enzyme detection system. The immunoglobulin isotype is revealed by self description. The isotype of Mab 4A12 was IgG2a and that of Mab 7B6 was determined to be IgG1a.

Example 4

Effect of Estrogen on NDP-Kinase/Nm23 Activity in Cytosolic and Stromal Cell Fractions from Primary Parental Breast Carcinoma Cell Lines Primary parental breast carcinoma cell lines were incubated with 100 nM 17-β-Estradiol for 24 hrs. Cells were incubated with cell media alone as a control. Cytosolic and stromal cell fractions were isolated as described by G. Pulido-Cejudo et al [1994, J. Chromatogr. B. 660: 37–47]. NDP-Kinase/Nm23 activity was determined in each cell fraction by anion-exchange high-performance liquid chromatography as described by G. Pulido-Cejudo et al. [1994, J. Chromatogr. B. 660: 37–47].

Isolated cytosolic and stromal cell fractions alongside purified NDP-Kinase/Nm23 from HL60 cells and recombinant Nm23-H1 were electrophoresed under non-denaturing conditions. Gels were electroblotted onto nitrocellulose membranes. Membranes were blocked with Tris-buffered saline (TBS) at 37° C. for 1 hr and probed with anti-NDP-Kinase/Nm23 (MAb 4A12) diluted 1:100 in TBS. Bands were visualized by incubating blots with goat-anti-mouse-alkaline-phosphatase diluted 1:500 in TBS followed by colourimetric detection in alkaline-phosphatase substrate buffer (pH 9.5) using BCIP and NBT as substrates.

Slab gels containing NDP-Kinase/Nm23 were run under non-denaturing conditions and stained for NDP-Kinase/Nm23 activity as described by Lam and Packham [1986, Biochem. Parmacol. 35: 4449–4455]. Samples containing NDP-Kinase/Nm23 were immunoprecipitated with the monoclonal antibody MAb 4A12 previously adbsorbed to protein-A-Sepharose beads. First, protein-A-Sepharose-MAb 4A12 immunoaffinity matrix was blocked for 2 hours with 10% FCS-RPMI 1640, and washed with 10 mM Tris-HCI pH8. Samples (100 p1) with a known NDP-Kinase/Nrn23 activity were incubated with either unreactive protein-A-Sepharose beads, or with protein-A-SepharoseMAb 4A12 matrix, and incubated overnight at 4° C. with constant stirring. Following incubation, the NDP-Kinase/Nm23 activity in the supernatant was determined as described by Larn and Packham [1986, Biochem. Parmacol. 35: 4449–4455].

As shown in Table 2, upon estrogen stimulation, the NDP-Kinase/Nm23 activity in the cytosolic fraction was nearly forty times more than that observed in the control. While estrogen exposure increases NDP-Kinase/Nm23 activity in the cytosol, the reverse effect is seen in the membrane bound NDP-Kinase/Nm23 activity.

TABLE 2

NPD-Kinase/Nm23 activity in stromal and cytosolic cell fractions

| Condition | NDP-Kinase/Nm23 Activity μmoles dATP/μg) | |
|---|---|---|
| | Stromal | Cytosolic |
| Control | $6.5 \pm 0.2 \times 10^{-1}$ | $1.8 \pm 0.2$ |
| Estrogen (100 nM) | $1.1 \pm 0.1 \times 10^{-2}$ | $44.8 \pm 2.1$ |

NDP-Kinase/Nm23 enzyme activities were determined as described by G. Pulido-Cejudo et al. [10].

The cell surface distribution of NDP-Kinase/Nm23 in intact cells was analysed. As shown in FIG. 1, Western Blots performed under nondenaturing PAGE, of either crude cytosolic preparations (lane 1) or purified NDP-Kinase/Nm23 from HL60 cells (lane 2) and recombinant Nm23-H1 (lane 3) show a similar electrophoretic profile, revealing a single homogeneous band in all samples using the antiNDP-Kinase/Nm23 MAb 4A12 monoclonal antibody.

Figure 2:
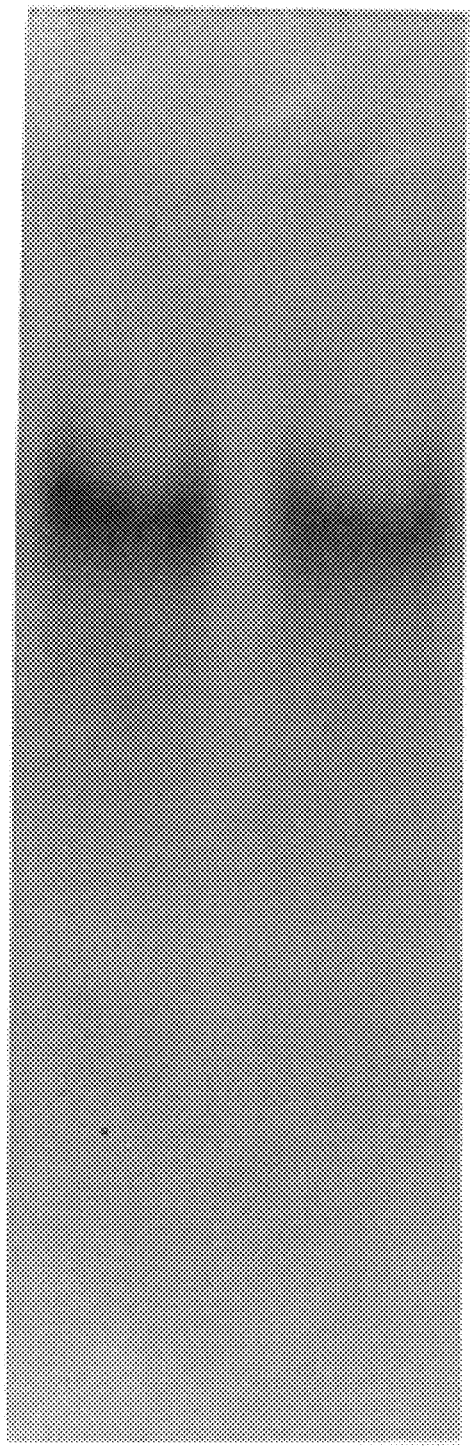
FIG. 2 shows the reactivity of anti-NDP-Kinase/Nm23 MAb 4A12 monoclonal antibody on crude cell extracts following non-denaturing PAGE. One crude cell extract was stained for NDP-kinase/Nm23 activity (lane 1) and another transferred to nitrocellulose and reacted with the anti-NDP-kinase/Nm23 Mab 4A12 monoclonal antibody (lane 2).

Further experiments were performed to characterize the identity of the protein bands recognized by MAb 4A12 on crude cell extracts following non-denaturing PAGE and transfer to nitrocellulose. As shown in FIG. 2, one sample was stained for NDP-Kinase/Nm23 activity (lane 1) and the second reacted with the anti-NDP-Kinase/Nm23 MAb 4A12 monoclonal antibody (lane 2). Protein bands containing NDP-Kinase activity (lane 1), ran at exactly the same position as those identified by Western blot using the monoclonal antibody MAb 4A12 (lane 2). Collectively, these results confirm the specificity of the monoclonal antibody MAb 4A12 and suggest that the latter antibody recognizes the active NDP-Kinase/Nm23 cytosolic oligomer. Finally, this antibody was used to study the cellular distribution of NDP-Kinase/Nm23 in peripheral blood cells isolated from both normal individuals and women with metastatic disease (lung/brain).

Example 5

Flow Cytometric Cellular Distribution of NDP-Kinase/Nm23 in Peripheral Blood Cells from Healthy Individuals and Women with Metastatic Breast Carcinomas Whole blood from normal and women with metastatic disease were spun at 1500 rpm in a refrigerated centrifuge for 10 min. at 4° C. The upper buffy coat was aspirated, diluted with an equal volume of PBS and applied onto Ficoll-Paque. Cells were spun at 1500 rpm for an additional 30 min. and PBMC collected at the interface. Cells were washed three times with PBS.

Whole blood cells were stained using a two colour immunofluorescence method. Briefly, 20 µl of MAb 4A12 antibodies (200 µg/ml), or control IgG1, was added to 100 µl of blood. Following an initial 30 min. incubation, the cells were washed and resuspended in 100 µl of cold PBS and goat-anti-mouse IgG-FITC-conjugated antibody was added. The mixture was incubated for 20 min., washed a subsequent time and cells were resuspended in 100 µl of PBS. Blood cells were thereafter incubated with 20 µl of one of the following phycoerythrin-conjugated mouse antibodies: IgG-PE (control); Leu 3-PE (anti-CD4); Leu2-PE (anti-CD8); Leu 4-PE (anti-CD3); Leu 12-PE (anti-CD19); Leullc-PE (anti-CD16); Leu 19-PE (antiCD56). After a 15 min. incubation, the erythrocytes were processed in an automated Q-prep workstation which sequentially delivers an erythrocyte lytic agent, a leukocyte stabilizer and a fixative. After erythrocyte lysis, cells were washed twice with PBS at 4° C. and fixed with 1 ml of 2% paraformaldehyde. The samples were analyzed in a flow cytometer equipped with an air-cooled argon ion laser operating at 10 mwatt. Simultaneous excitation of FITC and PE conjugates is achieved by fixing the excitation wavelength at 488 nm. Lymphocytes were clearly distinguished from monocytes and granulocytes on the basis of their forward light scatter (FAS) and side scatter light (SS) on a bivariant display. An electronic gate set around the cell population bearing the light scatter characteristics of granulocytes, monocytes and lymphocytes were activated for analysis.

Figure 3:
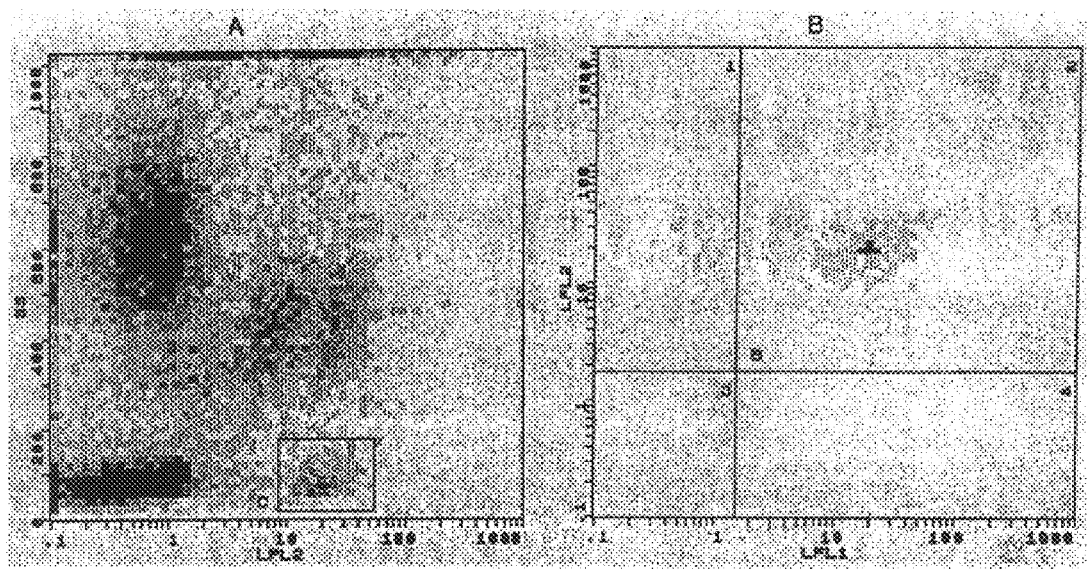
FIG. 3 shows a bivariant dot plot analysis of anti-CD19/anti-NDP-Kinase/Nm23 double-labelled peripheral blood cells from healthy women. Bivariant dot plot analysis (side scatter versus phycoerythrin labelled anti-CD19 [LF2]) was performed on double labelled PBMC's using Mab 4A12 as a secondary label detected with goat-anti-mouse FITC-antibodies. Control samples were reacted with control pre-immune IgG1 immunoglobulins followed by goat-anti-mouse IgG-FITC conjugated antibodies. Section I: Bivariant dot plot analysis on whole peripheral blood cells. Section IA: CD19+ labelled cells [LF2] were electronically gated and subsequently analyzed for their simultaneous activity against anti-NDP-Kinase/Nm23 Mab 4A12 monoclonal antibodies. As shown in Section IB, [LF2] anti-CD19+ cells plotted against LF1 anti-NDP-Kinase/Nm23 4A12 monoclonal antibodies show that approximately 93% of double labelled B-cells reacted against both anti-CD19 and anti-NDP-Kinase/Nm23 Mab 4A12 monoclonal antibodies (Section IB, quadrant 2). As shown in Section II, total lyphocytes reacted with control pre-immune IgG1 immunoglobulins remain unreactive whereas solely lymphocytes that have reacted with both anti-CD 19 and anti-NPD-kinase single out selectively labelled B-cells (Section II, anti-NDP/CD-19, quadrant 2).
Figure 3:
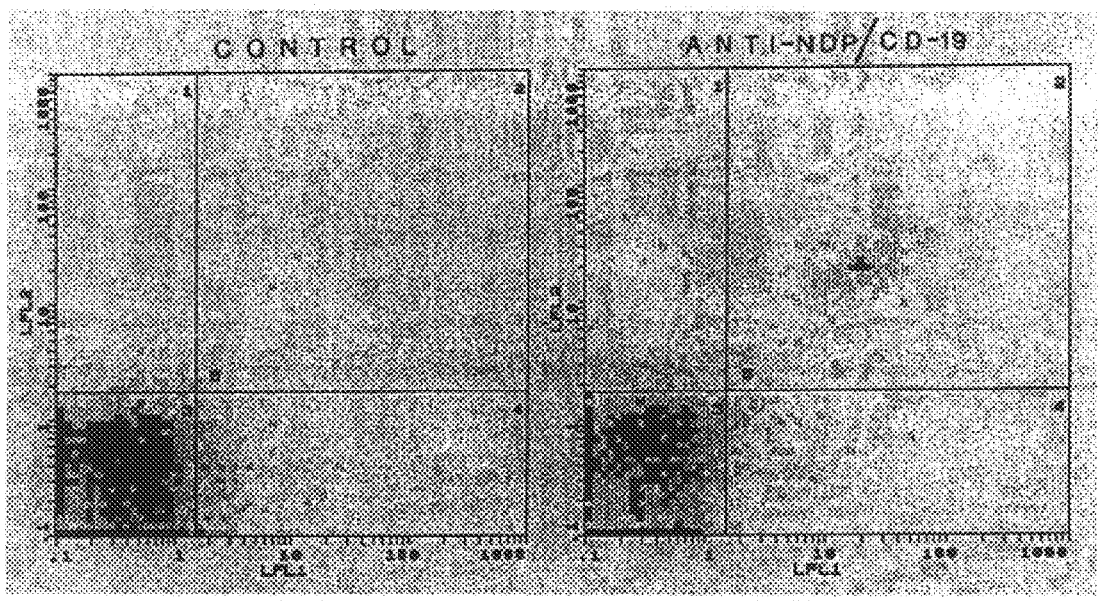

In the cell cycle, it has been proposed that the membrane-bound NDP-Kinase/Nm23 might modulate the activity of adenylate cyclase by replenishing GTP levels required for the activation of G proteins (Gs and Gl) which in turn mediate hormonal stimulation and inhibition of adenylate cyclase respectively [Kimura, N. and Shimada, N., 1983, J. Biol. Chem. 258: 2278–2283; Kimura, N. and Shimada, N., 1986, Biochem. Biophys. Res. Commun. 134: 928–936; Gilman, A. G., 1987, Ann. Rev. Biochem., 56: 615–649]. This observation prompted us to determine the reactivity of anti-NDP-Kinase antibodies (MAb 4A12) towards peripheral blood cells (PBMC). Two colour immunofluorescence studies were carried out using MAb 4A12 antibodies and various phycoerythrin-conjugated monoclonal antibodies, recognizing characteristic epitopes expressed by different subsets of lymphocytes. It was found that in PBMC's obtained from healthy women, only lymphocytes, carrying the CD19 integral membrane glycoprotein characteristic of B-cells (CD19+B cells), were simultaneously labelled with anti CD19 (FIG. 3, IA) and MAb 4A12 monoclonal antibodies (FIG. 3, IB). In this regard, close to 93% of CD19+ B-lymphocytes (as shown in the electronic gate of FIG. 3, IA) expressed the antigen recognized by MAb 4A12 in PBMC's isolated from healthy women (as shown in quadrant 2 of FIG. 3, IB as well as in FIG. 3, II, quadrant 2 labelled anti-NDP-CD19). In contrast, aprominent decrease in the double labelled CD19+-NDP-kinase$^+$-B-lymphocyte population was observed in women with metastatic disease (see Table 3).

TABLE 3

Percentage of double labelled anti-CD19/anti-NDP-Kinase circulating B-cells from peripheral blood

|  | % of anti-CD 19/anti-NDP-kinase Double labelled B-lymphocytes (B-gate) |
| --- | --- |
| Normal Subjects | 93.30 ± 1.02 |
| Women with Metastatic Disease (lung/Brain) | 2.91 ± 0.82 |

None of the other possible lymphocyte populations were selectively labelled with the monoclonal antibody raised against cytosolic NDP-Kinase/Nm23. Based on this analysis, it appears that the NDP-Kinase/Nm23 monoclonal antibody solely labels B-lymphocytes, most likely by reacting with the membrane-associated NDP-Kinase/Nm23 oligomer.

Example 6

ELISA Analysis of Human Breast Carcinoma Parental Cells

ELISA analysis of human breast carcinoma parental cell lines was conducted to demonstrate the reactivity of Mab 4A12 and Mab 7B6 against NDP-K and LAPase respectively. Briefly, 50000 parental cells were plated per well in a 96 well plate in RPMI 1640 medium+10% FCS+100 U/ml Penicillin+100 µg/ml Streptomycin. The plated cells were cultivated at 37° C., 5% $CO_2$, for 24 hours. The cell supernatants were removed, the cells were washed with PBS and subsequently fixed with 1% gluteraldehyde in PBS for 1 hour at room temperature. Washing with PBS occurred prior to blocking with casein for 1 hour at 37° C. 5% $CO_2$. Following another wash with PBS, serial dilutions of Mab 4A12 or Mab 7B6 were added to the wells and allowed to incubate for 2 hours at 37° C. 5% $CO_2$. Demonstration of the reactivity of Mab 4A12 and Mab 7B6 was evident upon the addition of a secondary antibody, anti-(IgG+IgM) peroxidase conjugated goat anti-mouse IgG+IgM (H+L) followed by the substate, OPD.

The summary of readings taken at 490 nm using Mab 7B6 against human LAP is shown below in Table 4.

TABLE 4

Summary of Reactivity of Mab 7B6 against LAP from Human Breast Carcinoma Parental Cells

| Mab 7B6 (ng/well) | Cell Line 1 OD 490 nm – Blank OD 490 nm | Cell Line 2 OD 490 nm – Blank OD 490 nm |
|---|---|---|
| 200 | 0.707 – 0.054 = 0.653 | 0.6 – 0.005 = 0.595 |
| 100 | 0.57 – 0.021 = 0.549 | 0.446 – 0.003 = 0.443 |
| 50 | 0.489 – 0.042 = 0.447 | 0.327 – 0.003 = 0.324 |
| 25 | 0.38 – 0.047 = 0.333 | 0.24 – 0 = 0.24 |
| 12.5 | 0.294 – 0.05 = 0.244 | 0.165 – 0 = 0.165 |
| 6.25 | 0.226 – 0.05 = 0.176 | 0.1 – 0.003 = 0.097 |
| 3.125 | 0.155 – 0.044 = 0.111 | 0.068 – 0.003 = 0.065 |
| 1.56 | 0.107 – 0.05 = 0.057 | 0.043 – 0.002 = 0.041 |
| 0.78 | 0.094 – 0.055 = 0.039 | 0.023 – 0.001 = 0.022 |
| 0.39 | 0.067 – 0.073 = 0 | 0.015 – 0 = 0.015 |
| 0.2 | 0.061 – 0.052 = 0.009 | 0.008 – 0 = 0.008 |
| 0.1 | 0.053 – 0.046 = 0.007 | 0 – 0 = 0 |

Example 7

NDP-Kinase/Nm23 and es-LAPase Actvities in Plasma of Women with Primary Breast Cancer NDP-Kinase/Nm23 and es-LAPase activities in plasma of relapsed patients with primary Breast Cancer compared to aged matched controls of otherwise healthy women, were determined by HPLC (Pulido-Cejudo et al. 1994, J. Chromatogr. B., 660:37–47) for NDP-Kinase/Nm23.es-LAPase activity was determined fluorometrically using leucine-β-naphthylamide as the substrate as described by Kuramochi et al. The reaction was stopped by boiling the samples at 100° C. for 10 mins, followed by centrifugation at 780×g at 4° C. for 10 mins. Values obtained represent the average of es-LAPase activity determined in triplicate in 16 patients from each test group.

NDP-Kinase/Nm23 and es-LAPase activities were determined using palsma immunoprecipitates obtained by immunoprecipitation using Covalent Mab 4A12$_{(IgG2a)}$-Protein G and LAPase Mab 7B6$_{(IgG1a)}$-Protein G matrices. Briefly, Plasma was spun at 500×g for 10 min. at 4° C. Plasma was removed by aspiration and spun once more at 500×g for 5 min. at 4° C. The resulting plasma was diluted 1:10 with PBS and 800 μl of plasma dilution was added to covalent Mab 4A12$_{(IgG2a)}$-Protein G and LAPase Mab 7B6$_{(IgG1a)}$-Protein G matrices containing 5 μg of antibody in 200 μl of beads pre-incubated with blocking buffer [50 mM Tris-HCl; 0.5% non-fat dry milk(NFDM)]. Samples were incubated at room temperature (~22° C.) for 15 min with constant gentle rotation in 0.5% BSA pre-coated Eppendorf tubes. After incubation samples were spun at 250×g Eppendorf-Microfuge at room temperature supernatants were removed. The beads containing the NDP-Kinase/Nm23 or es-LAPase activities were washed trice with PBS; 0.5% NFDM and finally resuspended in Calcium-free Hank's solution making up a 600 μl final reaction volume and 182 μM 1-leucine-β-naphthylamide. A corresponding blank of Mab 4A12$_{(IgG2a)}$-Protein G and LAPase Mab 7B6$_{(IgG1a)}$-Protein G-beads coated with 0.5% NFDM was used as baseline.

Plasma immunoprecipitates using MAb 4A12 (anti-NDP-Kinase/Nm23) and MAb 7B6 (anti-es-LAPase) consistently show higher levels of both estrogen dependent markers in women with non-invasive ductal and metastatic carcinomas when compared to plasma levels from otherwise healthy women. A summary of results obtained is set out in Tables 5 and 6.

TABLE 5 es-LAPase levels in plasma of women with Breast Cancer

| Patient Population (n = 100 per group) | LAPase Levels (μg/ml) |
|---|---|
| Normal | 5–10 |
| DCIS (non-invasive) | 450–600 |
| Metastatic (Lung/Brain) | 1200–3700 |

TABLE 6

NDP-Kinase/Nm23 levels in plasma of women with Breast Cancer

| Patient Population (n = 100 per group) | NDP-Kinase/Nm23 Levels (μg/ml) |
|---|---|
| Normal | 0.2–0.8 |
| DCIS (non-invasive) | 15–25 |
| Metastatic (Lung/Brain) | 500–890 |

Example 8

Flowcytometric Detection of Membrane-bound es-LAPase and NDP-Kinase/Nm23 in Epithelial Like Breast Carcinoma Parental Cells Obtained from Tumour Biopsies Indirect immunofluorescence staining of epithelial-like cells from tumour biopsies was performed by incubating adherent cells with human serum pre-adsorbed Mab 4 A12 or Mab 7B6 antibodies. Briefly, confluent cells were washed trice with PBS and incubated at 37° C. with 20 μl of Mab 4A12 or Mab 7B6 antibodies (200 μg/ml) or control mouse IgG1 in a final volume of 2 ml. After 20 min. incubation cells were washed trice once more with PBS and incubated with mouse anti-IgG-PE or mouse anti-IgG-FITC conjugtes for 15 minutes. Cells were subsequently washed three times with PBS, partially trypsinized and analyzed in a flowcytometer equipped with an air-cooled argon ion laser operating at 10 mwatt. Simultaneous excitation of FITC and PE conjugates was achieved by setting the excitation wavelength at 488 nm.

NDP-Kinase/Nm23 and es-LAPase levels in plasma of women with primary breast cancer compared to aged-matched controls of otherwise healthy women, were determined by ELISA using the monoclonal antibodies MAb 4 A12 and MAb 7B6 respectively.

Following purification of the monoclonal antibodies MAb 4A12 and MAb 7B6, their corresponding IgG2a (Anti-NDP-Kinase/Nm23) and IgG1(Anti-es-LAPase) isotypes were subsequently immobilized though a DSS cross-linking system obtained from Pierce (Rockford, Ill., U.S.A) according to the procedures described by the manufacturer.

MAb 4A12 and MAb 7 B6 Protein G matrices were used to selectively immunoprecipitate NDP-Kinase/Nm23 and esLAPase from plasma or cell membrane-bound fractions prior to determining their corresponding enzyme activities.

The results are shown in Table 7.

TABLE 7

NDP-Kinase/Nm23 activity in stromal and cytosolic cell Fractions from parental epithelial-like cells isolated from Tumour Biopsies of Women with Breast Carcinomas compared to women with beningn cysts/fibroadenomas

| Condition | NDP-Kinase/Nm23 activity ($\mu$moles dATP/$\mu$g) | |
| --- | --- | --- |
| | Stromal | Cytosolic |
| Fibroadenomas/Cysts | 80.24 ± 1.22 | 3.18 ± |
| DCIS (non-invasive) | 3.22 ± 0.12 | 25.34 ± |
| Metastatic (Lung/Brain) | 0.15 ± 0.04 | 102 ± 2.3 |

The scientific references, Patents and Patent applications referred to in the application are incorporated herein by reference.

The present invention is defined in terms of certain examples, which are not to be construed as limiting. The full scope of the present invention is defined in the following claims.

The embodiments of the invention in which an exclusive property of privilege is claimed are defined as follows:

1. A method of detecting breast cancer in a patient said method comprising:
   a) obtaining a blood sample from said patient;
   b) determining levels of nucleoside diphosphate kinase (NDP-kinase) and estrogen stimulated leucine amino peptidase (es-LAPase) in said blood sample using an immunoassay, wherein the levels of NDP-kinase are determined by an immunoassay using a monoclonal antibody produced by hybridoma cell line 4A12, deposited with the ATCC under Accession number CRL 11634, wherein said monoclonal antibody is specific for cytosolic and membrane bound NDP-kinase of human h160 cells,
   breast cancer in said patient being present when the levels of NDP-kinase and es-LAPase are higher than a predetermined threshold.

2. A method of detecting breast cancer in a patient said method comprising:
   a) obtaining a blood sample from said patient;
   b) determining levels of nucleoside diphosphate kinase (NDP-kinase) and estrogen stimulated leucine amino peptidase (es-LAPase) in said blood sample using an immunoassay, wherein the levels of es-LAPase are determined by an immunoassay using a monoclonal antibody produced by hybridoma cell line 7B6, deposited with the International Depositary Authority of Canada under Accession number IDAC 230300-1, wherein said monoclonal antibody is specific for es-LAPase,
   breast cancer in said patient being present when the levels of NDP-kinase and es-LAPase are higher than a predetermined threshold.

3. A method of detecting a metastatic breast cancer in a patient said method comprising:
   a) obtaining a blood sample from said patient;
   b) determining levels of nucleoside diphosphate kinase (NDP-kinase) and estrogen stimulated leucine amino peptidase (es-LAPase) in said blood sample using an immunoassay, wherein the levels of NDP-kinase are determined by an immunoassay using a monoclonal antibody produced by hybridoma cell line 4A12, deposited with the ATCC under Accession number CRL 11634, wherein said monoclonal antibody is specific for cytosolic and membrane bound NDP-kinase of human h160 cells,
   metastatic breast cancer in said patient being present when the levels of NDP-kinase and es-LAPase are higher than a predetermined threshold.

4. A method of detecting a metastatic breast cancer in a patient said method comprising:
   a) obtaining a blood sample from said patient;
   b) determining levels of nucleoside diphosphate kinase (NDP-kinase) and estrogen stimulated leucine amino peptidase (es-LAPase) in said blood sample using an immunoassay, wherein the levels of es-LAPase are determined by an immunoassay using a monoclonal antibody produced by hybridoma cell line 7B6, deposited with the International Depositary Authority of Canada under Accession number IDAC 230300-1, wherein said monoclonal antibody is specific for es-LAPase,
   metatstatic breast cancer in said patient being present when the levels of NDP-kinase and es-LAPase are higher than a predetermined threshold.

5. A diagnostic system for determining the level of NDP-kinase and es-LAPase in a blood sample using an immunoassay comprising a first monoclonal antibody produced by hybridoma cell line 4A12, deposited with ATCC under Accession number CRL 11634 which is specific for cytostolic and membrane bound NDP-kinase of h160 cells and a second monoclonal antibody produced by hybridoma cell line 7B6, deposited with the International Depositary Authority of Canada under Accession number IDAC 230300-1, which is specific for estrogen stimulated LAPase, wherein said diagnostic system is used for determining a state selected from the group consisting of breast cancer and metastatic breast cancer.

* * * * *

UNITED STATES PATENT AND TRADEMARK OFFICE
CERTIFICATE OF CORRECTION

PATENT NO. : 6,521,415 B1
DATED : February 18, 2003
INVENTOR(S) : Gabriel Pulido-Cejudo It is certified that error appears in the above-identified patent and that said Letters Patent is hereby corrected as shown below:

Column 6,
Line 48, change "CRL 11634" to -- HB 11634 --.

Column 15,
Line 12, change "CRL 11634" to -- HB 11634 --.

Column 21,
Line 35, change "CRL 11634" to -- HB 11634 --.

Column 22,
Lines 15 and 42, change "CRL 11634" to -- HB 11634 --.

Signed and Sealed this

Seventeenth Day of August, 2004

JON W. DUDAS
*Acting Director of the United States Patent and Trademark Office*